United States Patent
Leighton et al.

(10) Patent No.: US 11,762,813 B2
(45) Date of Patent: *Sep. 19, 2023

(54) QUALITY SCORE COMPRESSION APPARATUS AND METHOD FOR IMPROVING DOWNSTREAM ACCURACY

(71) Applicants: Bonnie Berger Leighton, Newtonville, MA (US); Deniz Yorukoglu, Cambridge, MA (US); Yun William Yu, Cambridge, MA (US); Jian Peng, Cambridge, MA (US)

(72) Inventors: Bonnie Berger Leighton, Newtonville, MA (US); Deniz Yorukoglu, Cambridge, MA (US); Yun William Yu, Cambridge, MA (US); Jian Peng, Cambridge, MA (US)

( * ) Notice: Subject to any disclaimer, the term of this patent is extended or adjusted under 35 U.S.C. 154(b) by 1051 days.

This patent is subject to a terminal disclaimer.

(21) Appl. No.: 16/267,778

(22) Filed: Feb. 5, 2019

(65) Prior Publication Data

US 2019/0171625 A1  Jun. 6, 2019

Related U.S. Application Data

(63) Continuation of application No. 14/697,114, filed on Apr. 27, 2015, now Pat. No. 10,198,454.

(60) Provisional application No. 61/984,743, filed on Apr. 26, 2014.

(51) Int. Cl.
| | | |
|---|---|---|
| *G06F 16/174* | (2019.01) | |
| *G16B 30/00* | (2019.01) | |
| *G16B 50/00* | (2019.01) | |
| *G16C 99/00* | (2019.01) | |
| *G16B 50/50* | (2019.01) | |
| *G16C 10/00* | (2019.01) | |
| *G16B 30/10* | (2019.01) | |

(52) U.S. Cl.
CPC ......... *G06F 16/1744* (2019.01); *G16B 30/00* (2019.02); *G16B 30/10* (2019.02); *G16B 50/00* (2019.02); *G16B 50/50* (2019.02); *G16C 10/00* (2019.02); *G16C 99/00* (2019.02)

(58) Field of Classification Search
None
See application file for complete search history.

(56) References Cited

PUBLICATIONS

Wandelt, "Data Management Challenges in Next Generation Sequencing," Datenbank-Spektrum, 12(3), 161-171, 2012.*

* cited by examiner

*Primary Examiner* — G. Steven Vanni
(74) *Attorney, Agent, or Firm* — David H. Judson

(57) ABSTRACT

This disclosure provides for a highly-efficient and scalable compression tool that compresses quality scores, preferably by capitalizing on sequence redundancy. In one embodiment, compression is achieved by smoothing a large fraction of quality score values based on k-mer neighborhood of their corresponding positions in read sequences. The approach exploits the intuition that any divergent base in a k-mer likely corresponds to either a single-nucleotide polymorphism (SNP) or sequencing error; thus, a preferred approach is to only preserve quality scores for probable variant locations and compress quality scores of concordant bases, preferably by resetting them to a default value. By viewing individual read datasets through the lens of k-mer frequencies in a corpus of reads, the approach herein ensures that compression "lossiness" does not affect accuracy in a deleterious way.

11 Claims, 5 Drawing Sheets

Modified Misra-Gries:

1. Initialize a primary hash map $A$.

Initialize 65535 hash sets $C_1,...,C_{65535}$.

Initialize the counter $D = 0$.

2. update( $i$ ): if $i \in A$, remove $i$ from $C_{A[i]}$, increment $A[i]$ (unless $A[i] = 65535$), and insert $i$ to the new $C_{A[i]}$.

else if $|A| < m$, insert $(i,1)$ into $A$ and insert $i$ into $C_1$.

else Remove an arbitrary element $j$ from $C_D$ (while $|C_D| = 0$, increment $D$ until nonempty). Remove $j$ from $A$. Insert $(i, D+1)$ into $A$ and $i$ into $C_{D+1}$.

3. query( $i$ ): if $i \in A$ then output $A[i] - D$.

else output 0

FIG. 3

QUALITY SCORE COMPRESSION APPARATUS AND METHOD FOR IMPROVING DOWNSTREAM ACCURACY

BACKGROUND OF THE INVENTION

Technical Field

This disclosure relates generally to next-generation sequencing (NGS) technologies and, in particular, technologies to store, transmit and process genomic data.

Background of the Related Art

Advances in next-generation sequencing (NGS) technologies have produced a deluge of genomic information, outpacing even increases in our computational resources. In addition to facilitating the widespread use of NGS data throughout biotechnology, this avalanche of data enables novel, large-scale population studies (e.g., maps of human genetic variation, reconstruction of human population history, and uncovering cell lineage relationships). To fully capitalize on these advances, however, better technologies to store, transmit, and process genomic data need to be developed.

The bulk of NGS data typically consists of read sequences, where each base call is associated with a corresponding quality score, which consume at least as much storage space as the base calls themselves. Quality scores are primarily used and often essential for assessing sequence quality, filtering low quality reads, assembling genomic sequences, mapping reads to a reference sequence, and performing accurate genotyping. Quality scores are a major bottleneck in any sequence analysis pipeline, impacting genomic medicine, environmental genomics, and the ability to find signatures of selection within large sets of closely-related sequenced individuals.

At the expense of downstream analysis, biomedical researchers have typically discarded quality scores or turned to compression, which has been moderately successful when applied to genomic sequence data. Quality score compression is usually lossy, meaning that maximum compression is achieved at the expense of the ability to reconstruct the original quality values. Due to decline in downstream accuracy, such methods are unsuitable for both transmission and indefinite storage of quality scores. To address these limitations, several newly-developed methods exploit sequence data to boost quality score compression using alignments to a reference genome, or use raw read datasets without reference alignment. Such solutions have not proven satisfactory. In particular, reference-based compression requires runtime-costly whole-genome alignments of the NGS dataset, while alignment-free compression applies costly indexing methods directly to the read dataset.

There remains a need to provide for an efficient and scalable method for very large (e.g., terabyte-sized) NGS datasets and that addresses the degradation of downstream genotyping accuracy that results from lossy compression.

BRIEF SUMMARY

Generally, this disclosure provides for a highly-efficient and scalable compression tool that compresses quality scores by capitalizing on sequence redundancy. In one embodiment, compression is achieved by smoothing a large fraction of quality score values based on k-mer neighborhood of their corresponding positions in the read sequences. The approach exploits the intuition that any divergent base in a k-mer likely corresponds to either a single-nucleotide polymorphism (SNP) or sequencing error; thus, a preferred approach is to only preserve quality scores for probable variant locations and compress quality scores of concordant bases, preferably by resetting them to a default value.

In particular, and to achieve scalable analyses, the approach herein preferably takes advantage of redundancy inherent in NGS read data. Intuitively, the more often a read sequence is seen in a dataset, the more confidence in its correctness; thus, its quality scores are less informative and useful. For longer read sequences (e.g., >100 bp), however, the probability of a read appearing multiple times is extremely low. For such long reads, shorter substrings (k-mers) can instead be used as a proxy to estimate sequence redundancy. By viewing individual read datasets through the lens of k-mer frequencies in a corpus of reads, the approach herein ensures that compression "lossiness" does not deleteriously affect accuracy.

The foregoing has outlined some of the more pertinent features of the disclosed subject matter. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the present invention and the advantages thereof, reference is now made to the following descriptions taken in conjunction with the accompanying drawings, in which:

FIG. 3 depicts a counting algorithm that is useful for generating a dictionary according to this disclosure.

DETAILED DESCRIPTION

For descriptive purposes, the compression tool of this disclosure is referred to as "Quartz" ("QUAlity score Reduction at Terabyte scale"), but this nomenclature is not intended to be limiting. Typically, the tool is implemented as computer software executing in one or more hardware processors. The computer software may be implemented as one or more programs, processes, instruction sets, execution threads, scripts, or the like.

According to this disclosure, the tool preferably compresses quality scores by capitalizing on sequence redundancy. Compression is achieved by smoothing a large fraction of quality score values based on the k-mer neighborhood of their corresponding positions in the read sequences. As is known, the term k-mer typically refers to all the possible substrings, of length k, that are contained in a string. In computational genomics, k-mers refer to all the possible subsequences (of length k) from a read obtained through DNA sequencing. As noted above, the technique herein is based on the intuition that any divergent base in a k-mer likely corresponds to either a SNP or sequencing error; thus, the tool preferably only preserves quality scores for probable variant locations and compress quality scores of concordant bases by resetting them to a default value. While k-mer frequencies have been used to infer knowledge about the error content of a read sequence (in known sequence-correction and assembly methods), they have not been used for quality score compression.

Figure 1A:
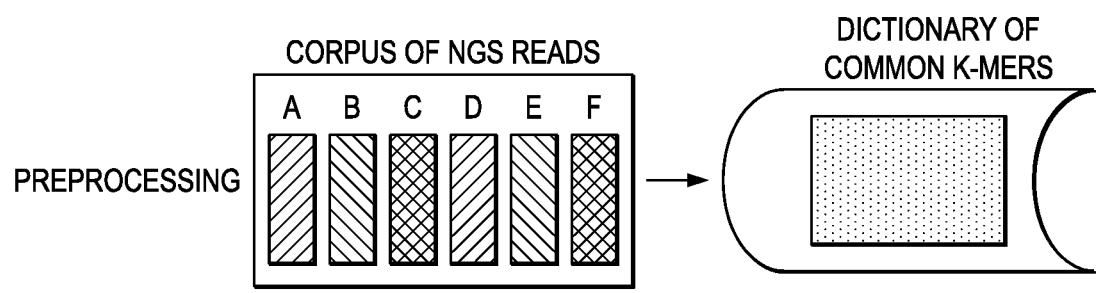
FIG. 1a depicts generation of a dictionary of common k-mers in a corpus of NGS reads.
Figure 1D:
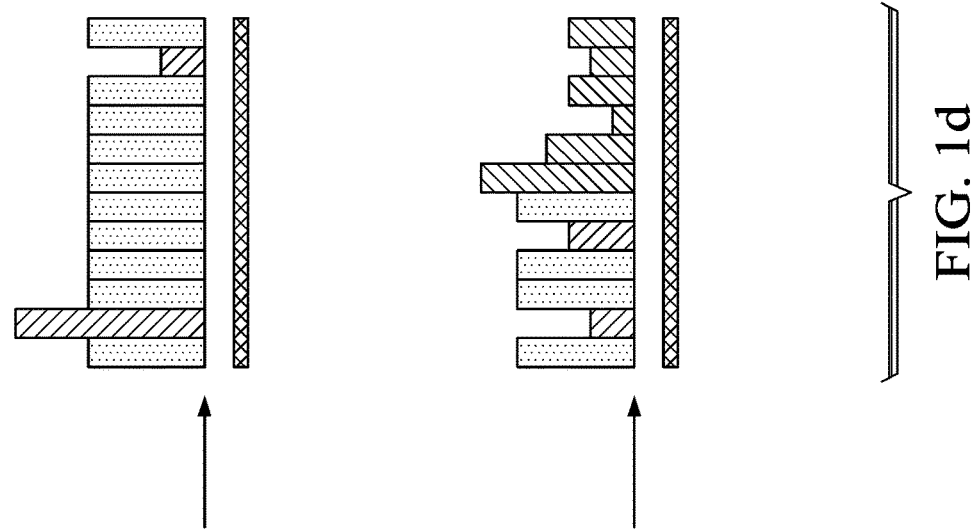
FIG. 1d depicts how quality scores are smoothed and the scores of all high-quality positions (i.e., bases) are set to a default value.
Figure 1C:
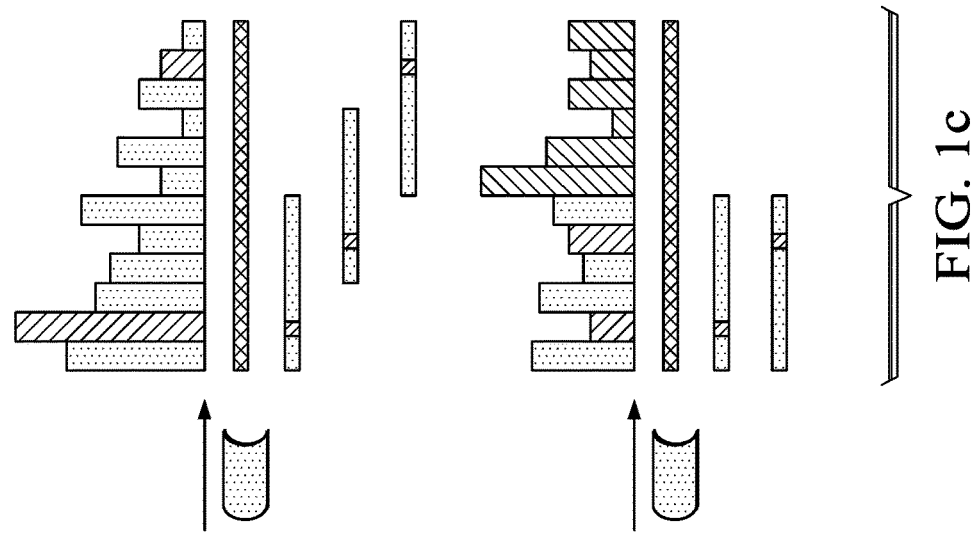
FIG. 1c depicts identification of a dictionary k-mers that are within one (for example) mismatch from the supporting k-mers.
Figure 1B:
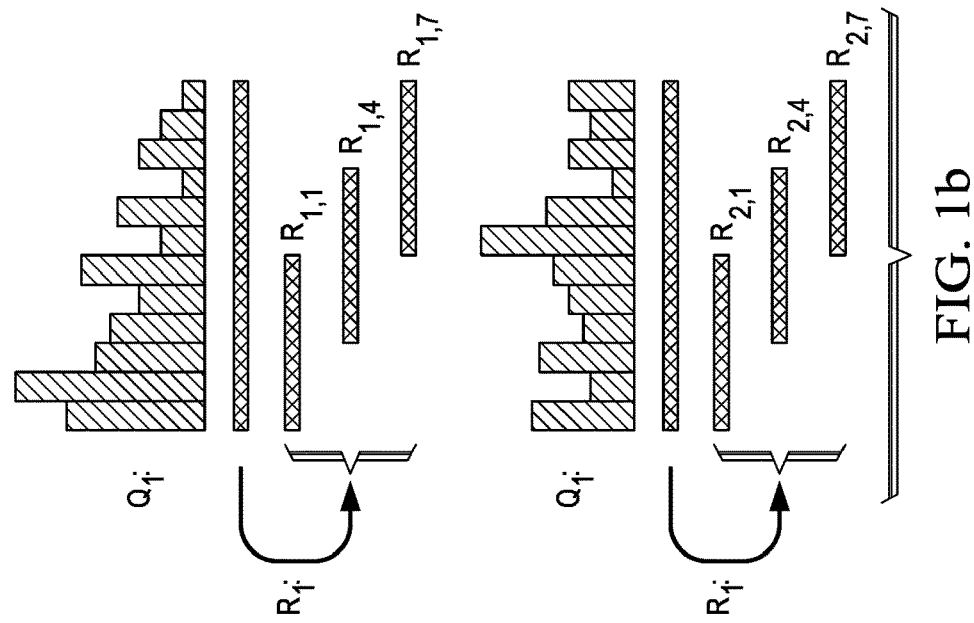
FIG. 1b depicts how each read sequence R is broken up into overlapping supporting k-mers.
Figure 1E:
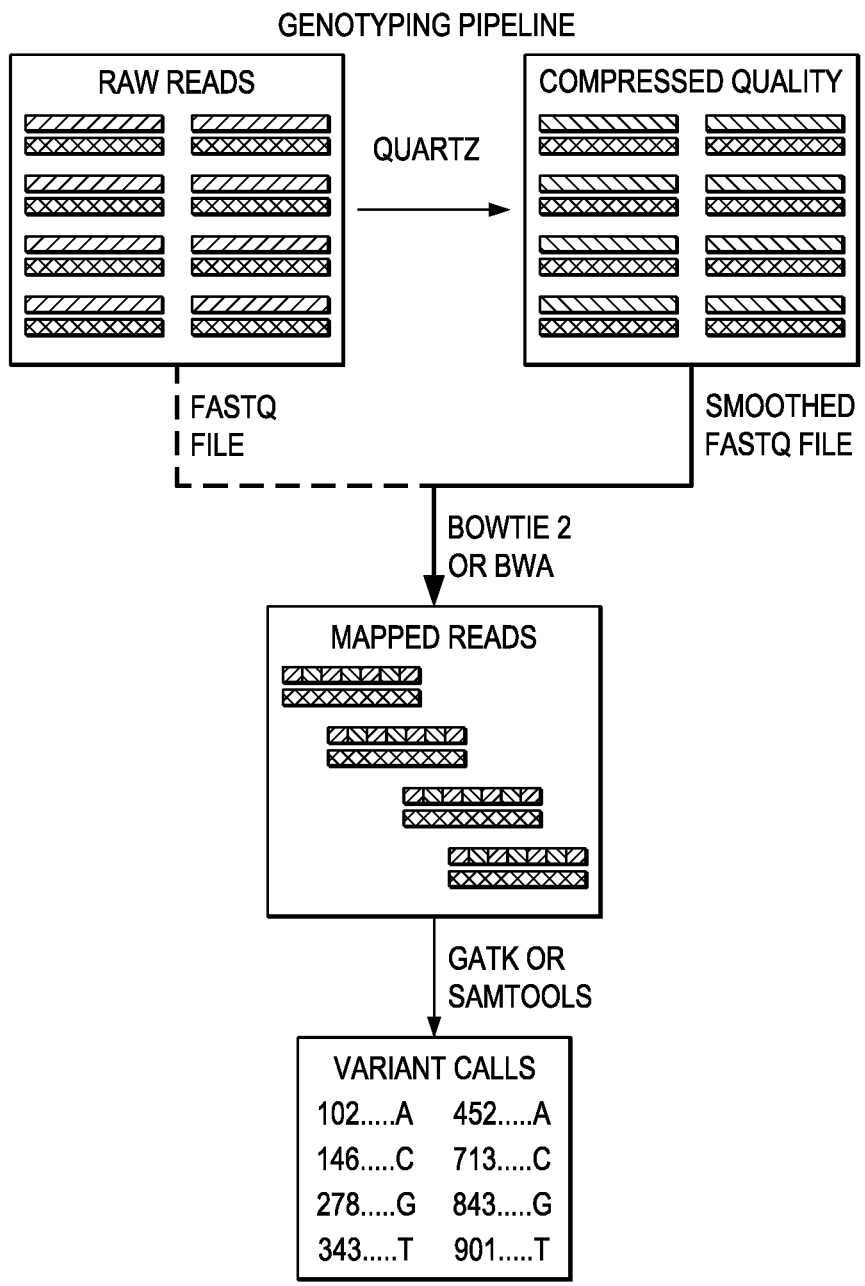
FIG. 1e depicts how tool of this disclosure is fit into an existing genotyping analysis pipeline, preferably as an additional processing step between acquisition of raw reads ad mapping and genotyping.

As seen in FIG. 1a, a dictionary of common k-mers in a corpus of NGS reads is generated. Typically, the dictionary is generated once for any species. At FIG. 1b, each read sequence R is broken up into overlapping supporting k-mers. At FIG. 1c, dictionary k-mers that are within one (for example) mismatch from the supporting k-mers are identified. Preferably, and as indicated at the top, every position different from a dictionary k-mer is annotated as a possible variant unless covered by a dictionary k-mer corresponding to a different supporting k-mer, in which case it will nevertheless be marked for correction. Other covered positions preferably are also marked for correction as high quality. As indicated at the bottom, when two dictionary k-mers correspond to the same supporting k-mer, preferably all mismatches are preserved, unless the mismatch portion is cover by a dictionary k-mer corresponding to a different supporting k-mer as shown (at top). Uncovered bases preferably also are annotated. At FIG. 1d, quality scores are smoothed and the scores of all high-quality positions (i.e., bases) are set to a default value. Scores of uncovered and possible variant loci are kept. At FIG. 1e, the tool is fit into an existing genotyping analysis pipeline, preferably as an additional processing step between acquisition of raw reads ad mapping and genotyping.

To generate the dictionary, in one embodiment a list of commonly occurring 32-mers in a population-size corpus of sequencing reads. For the corpus, and for exemplary purposes, 194 FASTQ files taken from the 1000 Genomes Project were used. This data corresponds to paired-end reads from 97 human individuals. Read lengths in the dataset ranged from 91-103 bp, with a total depth of coverage of about 700×. To construct the dictionary of k-mers memory efficiently, a counting algorithm depicted in FIG. 3 is used. This algorithm is a modified Misra-Gries approximate counting algorithm. It uses a collection of hash buckets instead of doubly-linked lists to minimize cache misses. The number of hash buckets is arbitrarily limited. Memory usage is controlled by maintaining an invariant that (for example) the total number of k-mers stored never exceeds a memory-usage parameter m. The approximation error is bounded by a decrement counter D. After partitioning the space of 32-mers into 256 subsets by the identity of the middle 4 bases, the algorithm was run in multiple passes on each of the subsets. By controlling the approximation ratio of the Misra-Gries algorithm, all 32-mers in the dictionary were guaranteed to occur at least 200 times in the corpus, and all 32-mers in the corpus that occurred at least 240 times were included in the dictionary.

The quality score compression may be carried out as follows. As input, the quality score compression algorithm Quartz requires a dictionary such as described above. Preferably, the dictionary comprises commonly-occurring k-mers extracted from a population-sized read dataset. Preferably, and as described above, the dictionary is designed in such a way that any given read dataset can be mostly covered from these k-mers within a small Hamming distance, or number of mismatches. Using this dictionary, the tool compresses the quality scores in any given read dataset by identifying k-mers from each read within a small Hamming distance from other k-mers in the dictionary. Any quality score value corresponding to a position that is concordant with at least one supporting k-mer is set to a default value, whereas the quality score value at any position that is divergent from all supporting k-mers is kept. This coarse representation greatly reduces the storage requirement for the quality scores of read datasets because the smoothed quality score values are substantially more compressible than the original values.

Although not intended to be limiting, because each read can be independently processed, the tool of this disclosure may be parallelized (e.g., using OpenMP), thereby achieving speedups nearly linear to the number of cores used, up to the I/O bound.

Parameter selection for the compression technique may be as follows. Efficiency concerns sufficiently dictate the parameters of k-mer length and Hamming distance that may be hard-coded optimal choices. Thus, for example, the k-mer length parameter, k, is 32 bp, although this is not a limitation as other lengths may be used. Typically, there are several criteria to consider when selecting the k-mer length within the Quartz quality score compression framework: (1) k-mers should be long enough to ensure that the number of all possible k-mers is much larger than the number of unique k-mers in the genome, so as to ensure incidental collisions between unrelated k-mers are rare; (2) because within the Quartz framework, k-mer neighbors preferably are defined to be within a Hamming distance of 1, k-mers should also be short enough to allow the probability that a k-mer contains more than one sequencing error to be low (this criterion is to ensure that k-mer sequences within reads originating from the same genomic region are highly likely to be detected as neighbors), and (3) k-mer length should ideally be a multiple of four, because a 4 bp length DNA sequence can be represented by a single byte. A 32 bp long k-mer satisfies all of these criteria. In particular, it is represented by a single 64-bit integer, with a relatively low probability of containing more than one sequencing error with Illumina sequences, as well as resulting in few k-mer collisions.

For the experimental results presented, a default replacement value (Q) for smoothed quality scores was selected as 50. In the datasets studied, the average quality score excluding the special value of 2, which was not modified, was at least 35. Preferably, and as noted above, Quartz only replaces a quality score within a 32-mer if all Hamming neighbors agree on a position. Thus, assuming that all 32-mers within a read are variants of 32-mers in the dictionary, the method only smoothes a quality score incorrectly if there are two read errors: one for the quality score and one at one of the other 31 locations. Then, as a first order approximation, the error probability for a smoothed location is $31 \times 10^{-3.5} \times 10^{-3.5} < 10^{-5}$, justifying the choice of Q=50. This parameter may be adjusted.

The following describes a Hamming neighbor search in one embodiment. As Hamming neighbors are defined as all k-mers in the dictionary that differ from a query k-mer by no more than 1 base substitution, the tool needs to be able to quickly search in the dictionary for all 3k+1 potential Hamming neighbors. To this end, a sorted list or hash tables may be used, but such techniques are CPU- or memory-inefficient, and they incur many cache misses. A preferred approach is to use locality sensitive hashing. Recall that an $(R, cR, P_1, P_2)$-sensitive LSH family F of hash functions h: M→S is defined if $\vee$p, q is a member of M, a uniformly random h is a member of F satisfies two conditions:

if $\|p-q\| \leq R$, then$(\text{Prob}(h(p)=h(q)) \geq P_1$, and  (1)

if $\|p-q\| \geq R$, then$(\text{Prob}(h(p)=h(q)) \leq P_2$.  (2)

Because the Hamming metric is discrete, all Hamming neighbors of a k-mer must match under one of the two projections. Thus, by double hashing, all Hamming neighbors can be found by looking in just two hash buckets, one for each hash function, giving much better cache-efficiency. Additionally, as genomic sequences are not chosen in an adversarial manner, instead of using random projections, projecting onto the front and back halves of the k-mer suffices in practice.

As the dictionary is static and read-only, both hash tables can be efficiently implemented by sorting lexicographically, first by the key (i.e. the projected half) and then by the rest, saving pointers to the first dictionary entry in each "bucket," and then discarding the projected half of each k-mer (as all k-mers are only accessed through the bucket pointers, the hash key is implied). This scheme also allows for binary search within each bucket, further speeding up lookups. For the default k=32, an array of length $2^{32}$ of unsigned 32-bit integers is used for the pointers, and an array of unsigned 32-bit integers of length |D|, the dictionary size, for the remaining half of the k-mers not specified by the pointers.

Thus, the technique described above provides for a highly-efficient and scalable compression tool that compresses quality scores by capitalizing on sequence redundancy. As described, compression is achieved by smoothing a large fraction of quality score values based on the k-mer neighborhood of their corresponding positions in the read sequences. The technique preferably exploits the fact that any divergent base in a k-mer likely corresponds to either a SNP or sequencing error; thus, the tool preferably only preserves quality scores for probable variant locations and compress quality scores of concordant bases by resetting them to a default value. Unlike other quality score compression methods, the tool and the approach herein maintains genotyping accuracy while achieving substantially higher compression ratios.

Generally, the compression is made possible by Quartz's coarse representation of quality scores, which allows it to store quality scores at roughly 0.4 bits per value (from the original size of 8 bits in FASTQ format).

Figure 2A:
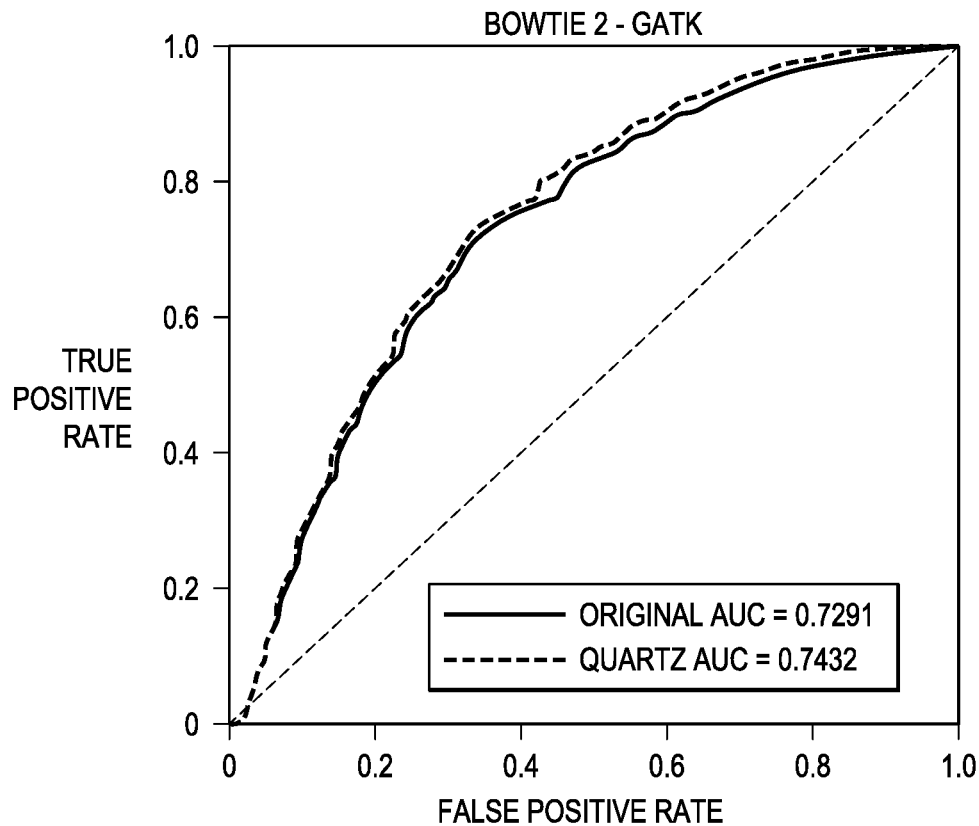
FIG. 2a illustrates a first scaled receiver operating characteristic (ROC) curve of genotyping accuracy according to the technique of this disclosure.
Figure 2B:
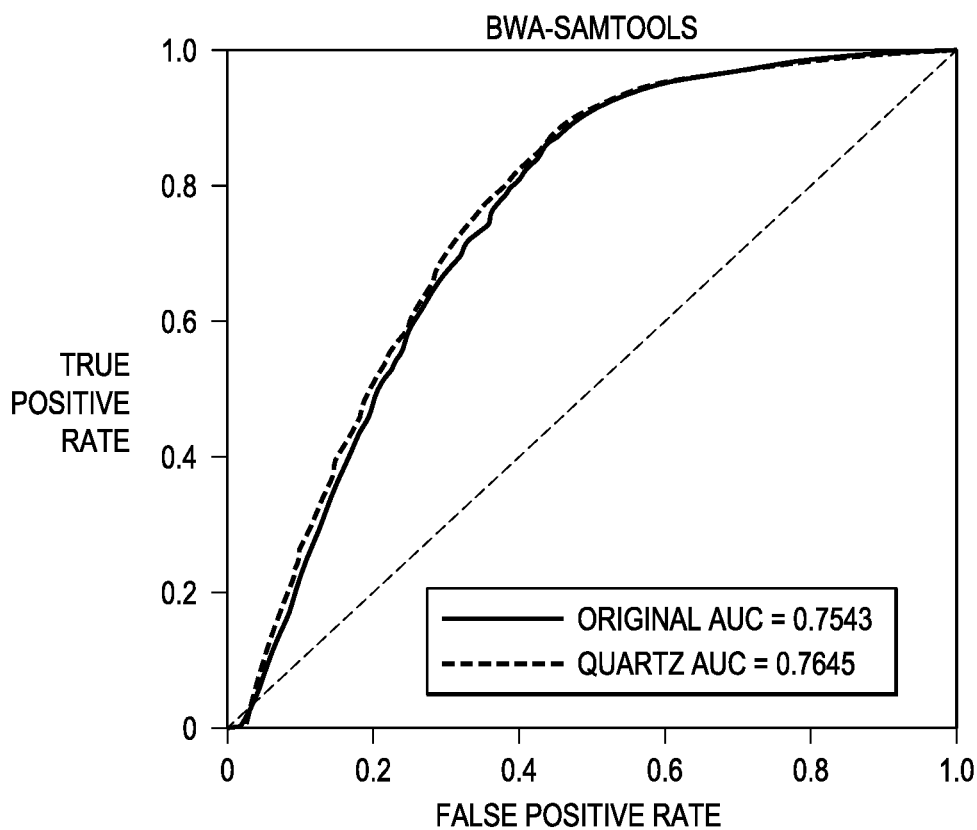
FIG. 2b illustrates a second scaled receiver operating characteristic (ROC) curve of genotyping accuracy according to the technique of this disclosure.

The above-described compression framework, despite eliminating a significant percentage (e.g., even more than 95%) of the quality score information, has been shown to achieve improved genotyping accuracy over the original, uncompressed quality scores, as compared to a trio-validated, gold-standard variant dataset for the NA12878 genome from the GATK "best-practices" bundle. In particular, both the GATK and SAMtools pipelines were applied to the compressed quality scores generated by Quartz on a gold standard NA12878 read dataset from the 1000 Genomes Project. The genotyping accuracy based on Quartz's compressed data consistently outperforms that based on the uncompressed raw quality scores as measured by the area under the receiver operating characteristic (ROC) curve. For the experiments, Quartz compression decreases the number of false positives in the million highest quality variant calls by over 4.5%. In FIG. 2, curves are shown for NA12878 before and after Quartz compression using (a) Bowtie 2 and GATK UnifiedGenotyper (FIG. 2a), and (b) BWA and SAMtools mpileup (FIG. 2b). Accuracy is improved using both variant-calling pipelines. Although this improvement is most pronounced for SNP calls, indel-calling accuracy is also maintained, if not improved, by Quartz compression. This result emerges from the discovery, through the application of Quartz, that quality score values within an NGS dataset are implicitly encoded in the genomic sequence information with 95% redundancy, so they often do not have to be stored separately. This improvement further indicates that the compression technique herein reduces the noise within the raw quality scores, thus leading to better genotyping results.

Quartz is highly scalable on large-scale, whole-genome datasets. After a one-time construction of the k-mer dictionary for any given species, quality compression is orders of magnitude faster than read mapping, genotyping, and other quality compression methods.

Additionally, Quartz is especially applicable for large-scale cohort-based sequencing projects because its improvements in genotyping accuracy are particularly useful for lower depths of sequencing coverage (e.g., 2×-4×).

Quartz alters quality scores and improves downstream genotyping accuracy, in common existing base quality score recalibration tools that make use of human genome variation from population-scale sequencing. Although currently-available recalibration tools and Quartz both use distilled information from a corpus of genomes, they differ in several key points. Most importantly, quality score recalibration tools do not apply compression; in fact, GATK recalibration tends to greatly increase the amount of storage needed. Quartz avoids losing compressibility, preferably by using a single default replacement quality value. Furthermore, because recalibration tools such as the GATK BaseRecalibrator, employ a list of known SNP locations, reads must first be mapped to the reference. As Quartz uses only k-mer frequencies and Hamming distances, it is possible to apply Quartz compression upstream of mapping, which is important when the task at hand either is assembly or mapping itself.

Quartz is a scalable, sequence-based quality compression method that can efficiently compress quality scores of tera-byte-sized and larger sequencing datasets, thereby solving both the problems of indefinite storage and transmission of quality scores. The experimental results further indicate that a significant proportion of quality score data, despite having been thought entirely essential to downstream analysis, are less informative than the k-mer sequence profiles, and thus can be discarded without weakening, and actually improving, downstream analysis. Thus, even with lossy data compression, it is possible to preserve biologically important data.

A Quartz compression step can be readily added to nearly any pre-existing NGS data processing pipeline. In one embodiment, and as described, Quartz takes as input a FASTQ file (the standard format for read data) and outputs a smoothed FASTQ file, which can in turn be input into any compression program (e.g., BZIP2 or GZIP) for efficient storage and transmission, or any read mapper (e.g., BWA or Bowtie 2). Further analysis steps such as variant calling (e.g., using SAMtools, GATK) can follow in the usual way.

With improvements in sequencing technologies increasing the pace at which genomic data is generated, quality scores will require ever greater amounts of storage space; compressive quality scores thus will become crucial to fully realizing the potential of large-scale genomics. The technique herein establishes that the twin goals of compression and accuracy do not have to be at odds with each other. Although total compression comes at the cost of accuracy, and quality score recalibration generally decreases compressibility, there is a happy medium at which one can get both good compression and improved accuracy. The techniques herein will greatly benefit any researchers who are generating, storing, mapping, or analyzing large amounts of DNA, RNA, Chip-seq, or exome sequencing data.

In summary, the technique described herein provides significant advantages for genomic data analysis. It provides for a tool to compress quality scores in a lossy manner, drastically reducing storage requirements while still preserving biologically important information. The automated approach not only preserves, but also improves, downstream genotyping accuracy. The tool thus provides broad applicability and can be readily incorporated into existing downstream analysis pipelines, at orders of magnitude faster speed than both mapping and variant calling. The tool addresses a critical and currently unmet need for reduced storage, increased transmission, and more efficient processing of next-generation sequencing reads, which will facilitate collaboration, enable even larger datasets, and allow future re-analyses on existing data.

While the disclosed subject matter will be described in the context of a method or process, the subject matter also relates to apparatus for performing the operations herein. This apparatus may be a particular machine that is specially constructed for the required purposes, or it may comprise a computer otherwise selectively activated or reconfigured by a computer program stored in the computer. Such a computer program may be stored in a computer readable storage medium, such as, but is not limited to, any type of disk including an optical disk, a CD-ROM, and a magnetic-optical disk, a read-only memory (ROM), a random access memory (RAM), a magnetic or optical card, or any type of media suitable for storing electronic instructions, and each coupled to a computer system bus. A given implementation of the disclosure is software written in a given programming language that runs in conjunction with a proxy on a standard Intel hardware platform running an operating system such as Linux. The functionality may be built into other code, or it may be executed as an adjunct to that code. A machine implementing the techniques herein comprises a processor, computer memory holding instructions that are executed by the processor to perform the above-described methods, functions or operations. Functions described herein may be implemented across multiple machines, processes, programs, systems and the like, co-located or remote from one another.

While given components of the system have been described separately, one of ordinary skill will appreciate that some of the functions may be combined or shared in given instructions, program sequences, code portions, and the like.

Processing (computation, storage or otherwise) as described herein may be implemented in whole or in part using cloud computing. As is well-known, cloud computing is a model of service delivery for enabling on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. Available services models that may be leveraged in whole or in part include: Software as a Service (SaaS) (the provider's applications running on cloud infrastructure); Platform as a service (PaaS) (the customer deploys applications that may be created using provider tools onto the cloud infrastructure); Infrastructure as a Service (IaaS) (customer provisions its own processing, storage, networks and other computing resources and can deploy and run operating systems and applications). A cloud platform may comprise co-located hardware and software resources, or resources that are physically, logically, virtually and/or geographically distinct. Communication networks used to communicate to and from the platform services may be packet-based, non-packet based, and secure or non-secure, or some combination thereof.

Thus, according to this disclosure, NGS quality scores are smoothed or removed, e.g., using one or more algorithms to determine which scores to remove, and based on sequence data, and at the same maintaining processing speed.

The techniques herein provide improved technologies to store, transmit and process genomic data.

The techniques herein provide for improvements to another technology or technical field, namely, next-generation sequencing (NGS), as well as improvements to the functioning of compression techniques.

Having described our invention, what is claimed follows below:

1. An apparatus, the apparatus being a computing machine, comprising:
   a hardware processor;
   computer memory holding computer program instructions executed by the processor to process genomic data, the computer program instructions comprising program code configured to:
     receive, as a dictionary, a set of data comprising commonly-occurring k-mers extracted from a read dataset;
     compress Next Generation Sequencing (NGS) quality scores in a given read dataset by identifying k-mers from each read within a given mismatch distance from other k-mers in the dictionary to generate compressed quality scores, wherein the dictionary has the property that any given read dataset is covered from k-mers within a given Hamming distance; and
     provide the compressed quality scores to a genotyping analysis pipeline;
     wherein processing efficiency in the computing machine is improved by identifying the quality scores within the given Hamming distance using a cache-efficient hash function.

2. The apparatus as described in claim 1 wherein the program code configured to compress the NGS quality scores comprises program code further configured to:
   set to a default value any quality score value corresponding to a position that is concordant with at least one supporting k-mer; and
   save the quality score value at any position that is divergent from all supporting k-mers.

3. The apparatus as described in claim 1 wherein the read dataset is a dataset associated with a population.

4. The apparatus as described in claim 1 wherein the program code is further configured to generate the dictionary.

5. The apparatus as described in claim 1 wherein the program code configured to compress NGS quality scores comprises program code further configured to:
   break a read sequence in the read dataset into overlapping k-mers;

with respect to the read sequence, identify k-mers in the dictionary that are within a given mismatch distance from supporting k-mers; and annotate a position different from a dictionary k-mer as a possible variant unless covered by a dictionary k-mer corresponding to a different supporting k-mer.

6. The apparatus as described in claim 5 wherein the program code is configured to preserve all mismatches when two dictionary k-mers correspond to the same supporting k-mer unless a mismatch portion is covered by a dictionary k-mer corresponding to a different supporting k-mer.

7. The apparatus as described in claim 6 wherein the program code is further configured to:

smooth the quality scores; and set positions exhibiting a given quality value to a default value while retaining scores of uncovered and possible variant loci.

8. The apparatus as described in claim 1 wherein compression of the NGS quality scores is lossy.

9. The apparatus as described in claim 1 wherein the program code is further configured to perform an additional compression of the compressed quality scores.

10. The apparatus as described in claim 1 wherein the program code is further configured to generate the dictionary using a counting algorithm and a collection of hash buckets.

11. A method for improving a genotyping analysis pipeline comprising read dataset acquisition and genotyping, comprising:

configuring a quality score compression tool between the read data acquisition and the genotyping, the quality score compression tool comprising computer software executing in one or more hardware processors, the computer software comprising program code executed in the one or more hardware processors to:

receive, as a dictionary, a set of data comprising commonly-occurring k-mers extracted from the read dataset;

compress quality scores in a given read dataset by identifying k-mers from each read within a given mismatch distance from other k-mers in the dictionary to generate compressed quality scores, wherein the dictionary has the property that any given read dataset is covered from k-mers within a given Hamming distance; and provide the compressed quality scores for the genotyping.

* * * * *